(12) United States Patent
Lob et al.

(10) Patent No.: US 6,238,436 B1
(45) Date of Patent: *May 29, 2001

(54) MODULAR ARTIFICIAL HIP JOINT

(75) Inventors: Günter Lob, München; Hans-Joachim Fischer, Berlin; Gerd Steür, Berlin; Curt Kranz, Berlin, all of (DE)

(73) Assignee: Biomet, Merck Deutschland GmbH, Berlin (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/836,707

(22) PCT Filed: Nov. 20, 1995

(86) PCT No.: PCT/DE95/01653

§ 371 Date: Aug. 6, 1997

§ 102(e) Date: Aug. 6, 1997

(87) PCT Pub. No.: WO96/15738

PCT Pub. Date: May 30, 1996

(30) Foreign Application Priority Data

Nov. 19, 1994 (DE) ................................. 44 42 205

(51) Int. Cl.⁷ ........................................................ A61F 2/36
(52) U.S. Cl. .................................... 623/22.42; 623/23.18
(58) Field of Search ............ 623/23, 18, 20 (U.S. only), 623/20.15, 21.17, 22.12, 22.41–22.46, 23.18, 23.44, 23.45, 19.11–19.14, FOR 19, FOR 16

(56) References Cited

U.S. PATENT DOCUMENTS

| 4,865,609 | * | 9/1989 | Roche | 623/23 |
| 5,002,578 | | 3/1991 | Luman | |
| 5,194,066 | * | 3/1993 | Van Zile | 623/20 |
| 5,489,311 | * | 2/1996 | Cipolletti | 623/20 |

FOREIGN PATENT DOCUMENTS

| 94 18 963 U | 3/1995 | (DE) . |
| 0135755 | 4/1985 | (EP) . |
| 0163121 | 12/1985 | (EP) . |
| 0190981 | 8/1986 | (EP) . |
| 0243298 | 10/1987 | (EP) . |
| 0359457 | 3/1990 | (EP) . |
| 0399920 | 11/1990 | (EP) . |
| 0498518 | 8/1992 | (EP) . |
| 0634154 | 1/1995 | (EP) . |
| 2575383 | 7/1986 | (FR) . |
| 2629707 | 10/1989 | (FR) . |

* cited by examiner

Primary Examiner—David H. Willse
(74) Attorney, Agent, or Firm—Venable; Robert Kinberg; Catherine M. Voorhees

(57) ABSTRACT

A modular artificial hip joint includes a head part and at least one shaft part. The shaft part, which can be driven into the bone and forms the distal region, is connected to the distal end of the head part by insertion, preferably by means of an insert cone. A first screw or tie rod, guided through an axial bore in the head part, can be screwed into the threaded bore in the shaft part. In order to guide a second screw for separating the conical insert connection between the individual components of the artificial joint, the bore in the head part is threaded and has a diameter which is greater than the diameter of the threaded bore in the shank part.

8 Claims, 4 Drawing Sheets

MODULAR ARTIFICIAL HIP JOINT

BACKGROUND OF THE INVENTION

The invention relates to a modular joint prosthesis having a head part and at least one shaft part which are insertably connectable with one another by means of a cone connection.

Such joint prostheses are produced in the most various shapes and sizes, to enable the most precise possible adaptation to the shape of the bone of a particular patient, as well as the current status of the bony tissue, taking the clinical picture into account.

By means of a multi-part embodiment with nonpositive connection of the corresponding individual parts in the proximal region, the adaptation can be accomplished optimally. At the same time, positioning of the joint head is possible regardless of the shaft diameter.

From European Patent Disclosure EP-B1 0 243 298, a kit for a shaft prosthesis is known, which has a head part that can be provided with a joint ball, an end part anchored in the bone, and an intermediate part that can be positioned between the two. All the parts have conical bores or complementary pegs, and as a result the prosthesis can be assembled by making conical insert connections. The head part and intermediate part each have an axial through bore.

The end part is provided with releasable engagement means, for the sake of transmitting a force in the axial direction. When the individual parts are put together, the corresponding bores are aligned axially in the direction of the shaft. The individual parts of the prosthesis are put together using a tie rod that transmits a force in the axial direction and that penetrates both the head part and succeeding shaft parts and can be screwed into the threaded bore of the end part. As a result, the head part, or the intermediate part, and the end part are firmly tightened against one another, so that loosening of the individual parts of the prosthesis from the mechanical strain during use need not be feared.

The above-described embodiment has the disadvantage that in such a prosthesis, the insert connection between the individual parts cannot be undone or released in the implanted state, even though this is sometimes necessary for medical reasons—for instance for resetting or replacing the head part. The conical insert connections, even after prior removal of the tie rod provided in the interior of the shaft, are held together so firmly that, if disassembly becomes necessary, damage to the femur or at least undesired loosening of the shaft is sometimes unavoidable, which is detrimental to the patient.

SUMMARY OF THE INVENTION

In view of the deficiencies in the prior art, it is the object of the invention to create a modular joint prosthesis of the generic type described at the outset, which in a simple way allows the individual elements to be loosened from one another, even from the outside.

This object is attained according to the invention by providing a bore that extends essentially coaxial to the longitudinal axis of a shaft part of a modular joint prosthesis and through the head part of the modular joint prosthesis and at least one section of the shaft part, the bore having a first segment with a first diameter and a first thread in the head part and a second segment in the shaft part with a second thread part and a second diameter, where the first diameter is greater than the second diameter so that an insert connection between the head part and the shaft part can be released.

The invention encompasses the recognition that with a screw bolt, considerable pressure forces can be generated in the axial direction if the end of the bolt is braced against an abutment. To that end, the edge of the bore of a succeeding shaft element is also suitable, on the condition that the outer diameter of a bolt to be screwed into the threaded bore is greater than the inside diameter of the succeeding element. Since replacement, especially of the head element, may become advisable (in advanced disease or for other indications), the succeeding elements may have a bore of constant diameter; in that case, the last (distal) element optionally has a thread that has a tie rod for connecting the shaft elements or setting the cone elements. The exertion of force for loosening two successive elements can be achieved all the more conveniently, the less its pitch is selected to be.

It is especially advantageous in the invention that without removing the lower part of the shaft, which remains in the bone space, the head part near the joint can be removed and replaced if needed. This is associated with substantially less stress on the patient than in conventional prostheses. Moreover, with the head part removed the corresponding interior of the bone is also accessible for other therapeutic purposes. "Head part" in the present afflication is understood to mean the part of the prosthesis near the joint, a part that can also be advantageously used in the case of joint replacement in other regions of the body.

Prosthesis shafts embodied as a modular system have, at least as the head part and end part, a system of various individual elements of different sizes, which are preferably joined together by putting together their proximal or distal ends that have corresponding conical pegs or recesses. The requisite stability of the insert connection is assured by screw means—preferably embodied as a tie rod. The end part is embodied as a hollow shaft, and the axially extending longitudinal bore of the carrier part has a thread on its proximal end portion. The tie rod is guided through a cylindrical channel, located on the same axis as the longitudinal bore in the carrier part, in the head part and screwed into the end part, which is provided with a thread.

According to the preferred embodiment of the invention, at least part of the cylindrical channel in the head part of the modular hip prosthesis shaft is embodied as a threaded bore. This threaded bore has a diameter which is greater than the diameter of the threaded bore, receiving the tie rod, in the succeeding shaft part. This diameter relationship advantageously assures that when the prosthesis parts have been put together, a free area remains on the proximally provided, frustoconical end of the succeeding shaft part, this free area being an essentially circular-annular top face of the truncated cone. This face region is available as an abutment for a screw bolt, which can be screwed into the head part once the tie rod is removed. The bolt screwed into the head part is braced on the substantially circular-annular abutment. Upon a further screwing motion, an axial pressure force is favorably generated, which releases the firm conical insert connection (despite the absence of the tie rod) between the head part and the succeeding shaft part enough that the head part can be removed for replacement purposes, or can be swiveled to the desired extent with regard to the succeeding shaft part on its frustoconical peg provided on the proximal end. To assure an adequately large abutment area for force transmission when the connection between the head part and the succeeding shaft part is loosened or released, a diameter ratio between the bores in the head part and the succeeding shaft part in the range from 1.5 to 2.5 is favorable.

In another advantageous further feature of the invention, the thread provided for the screw bolt extends in the head part of the modular hip prosthesis shaft over the entire length of the available cylindrical channel. For both the threaded bore in the head part of the hip prosthesis shaft and for the threaded portion on the proximal end of the succeeding shaft part, a metric thread is provided. The thread in the head part preferably has a lesser pitch than the thread on the proximal end of the succeeding shaft part and thereby makes it easier to generate the pressure force, by means of the screw bolt, that is required to loosen the firm conical insert connection.

In a further advantageous feature of the invention, the described provisions can be employed, using various graduations, multiple times in successive elements with one and the same modular shaft. In the description made here, the term "head part" would merely then be replaced by the phrase "preceding shaft element in the distal direction". It can be seen that the graduations in diameter of the bores each increase in the distal direction.

In an additional further feature of the invention, the proximal end of the threaded bore provided in the succeeding shaft part has a recess, which is favorably embodied as a chamfer arranged symmetrically to the longitudinal axis of the bore. It is thus advantageously achieved that the screw bolt, whose free end is likewise chamferred at the same angle, when braced upon the proximal end of the supporting part cannot enter into operative contact with the thread of the threaded bore provided in this region, and thus when the pressure force required to loosen the conical insert connection between the head part and the succeeding shaft part is generated, deformation of the first courses of the thread is avoided. A deformed thread would make it impossible to screw the tie rod back into the proximal end of the succeeding shaft part after adaptation or replacement of the head part. For introducing the force into the abutment, an angle of inclination of the chamfer in the range from 45° with respect to the center axis of the corresponding threaded bore is favorable.

The head part, on its medial side, below the cone for the joint connection, has a channel recess, which favorably forms an engagement and support region for a tool that is inserted to swivel or pull off the head part, once the cone connection between the head part and the succeeding shaft part has been released as described above.

To assure the maximum possible adaptation of the joint shaft to the anatomical conditions of a patient, a kit with differently embodied head parts and succeeding shaft parts for producing an individually adapted shaft is advantageous. The individual parts of the hip joint shaft differ in diameter, length and curvature. They can be combined with one another, on the condition of their having an adapted outer diameter.

BRIEF DESCRIPTION OF THE DRAWINGS

Other advantageous further features of the invention are defined by the dependent claims and will be described in further detail below, together with the description of the preferred embodiment of the invention, in conjunction with the drawings in which:

Fig. 1$a$ is the sectional view taken along the line 1$a$ . . . 1$a$ of FIG. 1;

DETAILED DESCRIPTION OF THE INVENTION

Figures 1, 1A:
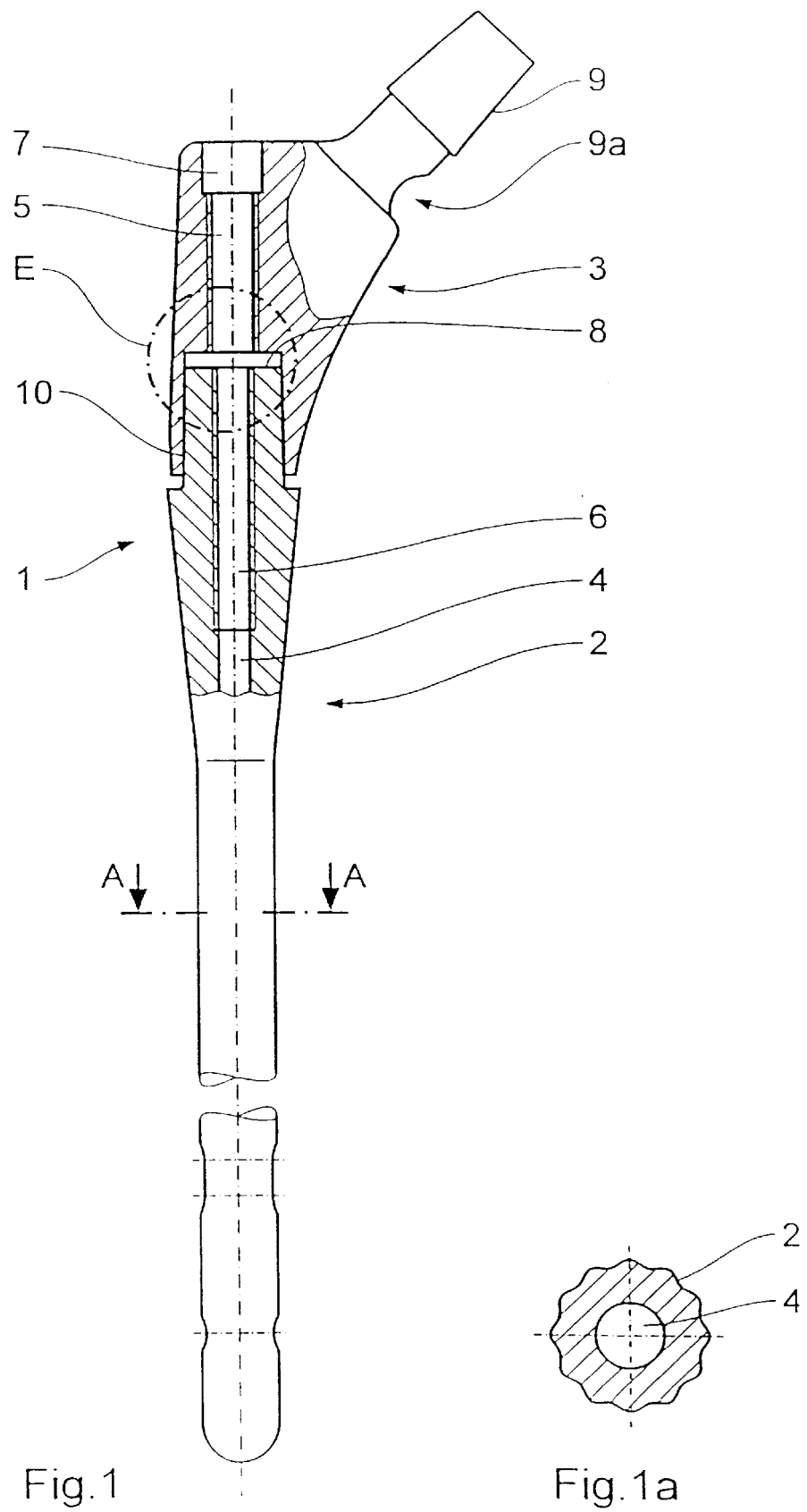
FIG. 1 is a the preferred embodiment of the invention in a schematic fragmentary sectional view.
Figure 2:
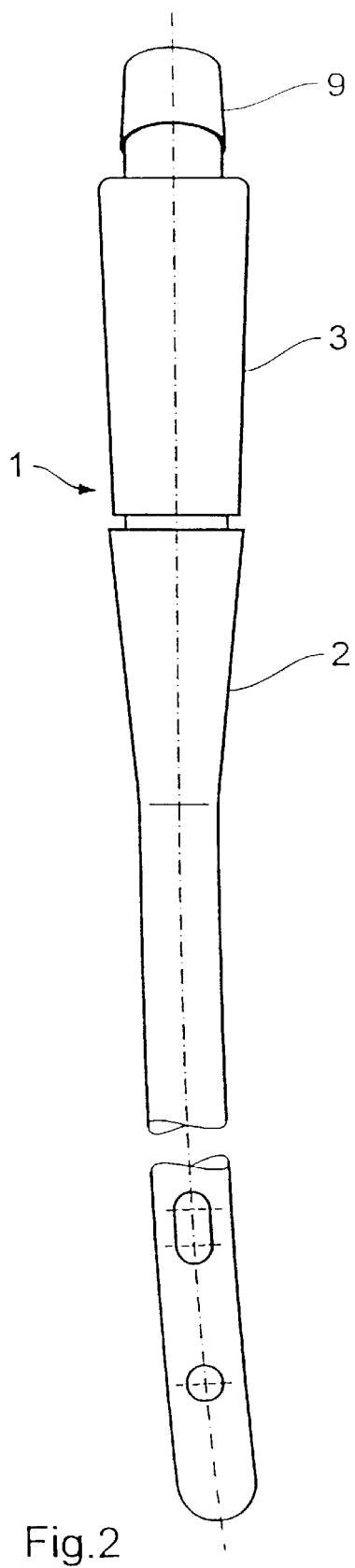
FIG. 2 is a simplified view of the preferred embodiment of the invention of FIG. 1, in a side view seen from the left.
Figure 4:
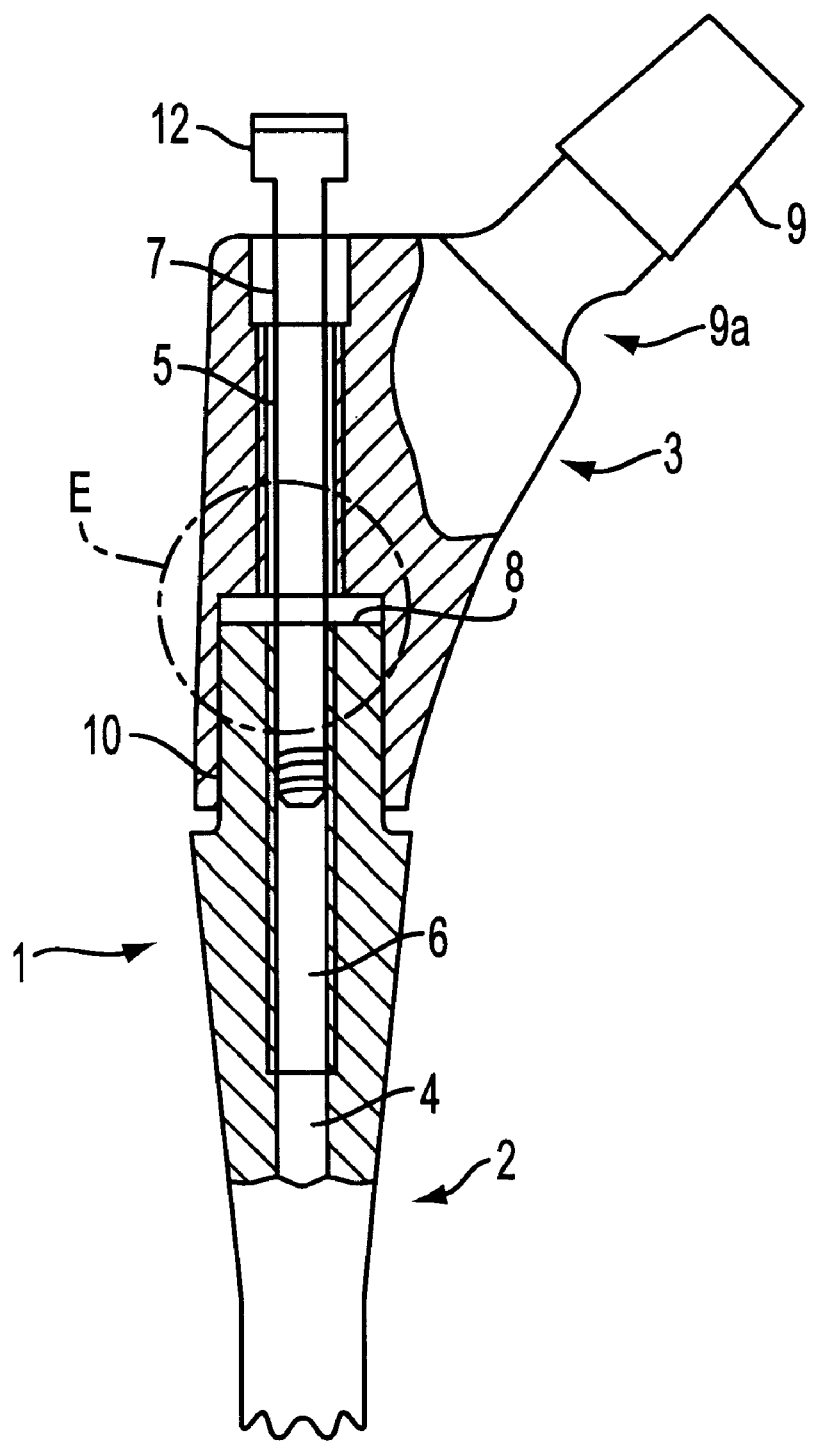
FIG. 4 shows a tie rod being screwed into a bore of the preferred embodiment of FIG. 1.

The modular joint prosthesis 1, shown in FIGS. 1, 1$a$ and 2 in the form of a side view, a section, and a fragmentary section, comprises a shaft part 2 and a head part 3, each of which have profiling in the longitudinal direction. The individual parts 2 and 3 of the shaft 1 are joined together, located on the same axis and pivotable relative to one another, by means of a conical insert connection 10. For "setting" the cone and securing this insert connection against axial loosening, a tie rod is provided, which is passed through the channel 12, embodied as a threaded bore, of the head part 3 and screwed into the proximal region, embodied as a threaded bore, of the channel 4 provided in the succeeding shaft part 2 FIG. 4. The screw insertion proceeds far enough that the proximal end of the tie rod is braced in the recess 7, and the individual parts 2 and 3 of the modular hip prosthesis shaft 1 are moved axially toward one another, until the conical insert connection 10 has the desired strength.

In order to be able to vary the position of the head part 3 which has a joint connection cone 9, relative to the succeeding shaft part 2 or to replace the head part 3, the conical insert connection 10 must be loosened again. After the tie rod, 12 is loosened and removed by twisting, a screw bolt (not shown) is screwed into the threaded bore 5 of the head part 3. Since the diameter $D_1$ of the threaded bore 5 in the head part 3 has a greater value than the diameter $D_2$ of the proximal portion 6, provided with a thread, of the central bore 4 of the succeeding shaft part 2, the screw bolt is based against a circular ring, whose area is defined by the difference in diameter $D_1$–$D_2$, on the top face 8 of the proximal end, embodied as a truncated cone, of the head part 3 and is thus capable of generating an axially oriented pressure force. This force releases the insert connection 10, which is very firm after the "setting" of the cone, and conveniently makes it possible to readapt the hip prosthesis shaft 1 to a patient's altered physical conditions.

The channel recess 9$a$ provided on the medial side of the head part 3 below the joint connection cone 9 serves as an engagement point for a tool, with which the head part 3 after the conical insert connection 10 between the head part and the succeeding shaft part has been loosened again, can be pivoted on the same axis or pulled off the succeeding shaft part if needed.

In this connection, it has proved favorable for the manipulability of the means for generating the pressure force required to loosen the conical insert connection to provide a diameter ratio of the bores 4, 5 in the range from 1.5 to 2.5, and to provide the bore 5 with a thread over its entire length. Metric threads are preferably used; the thread of the threaded bore 5 in the head part 3 has a lesser pitch than the thread in the proximal portion 6 of the bore 4 of the succeeding shaft part 2.

Figure 3:
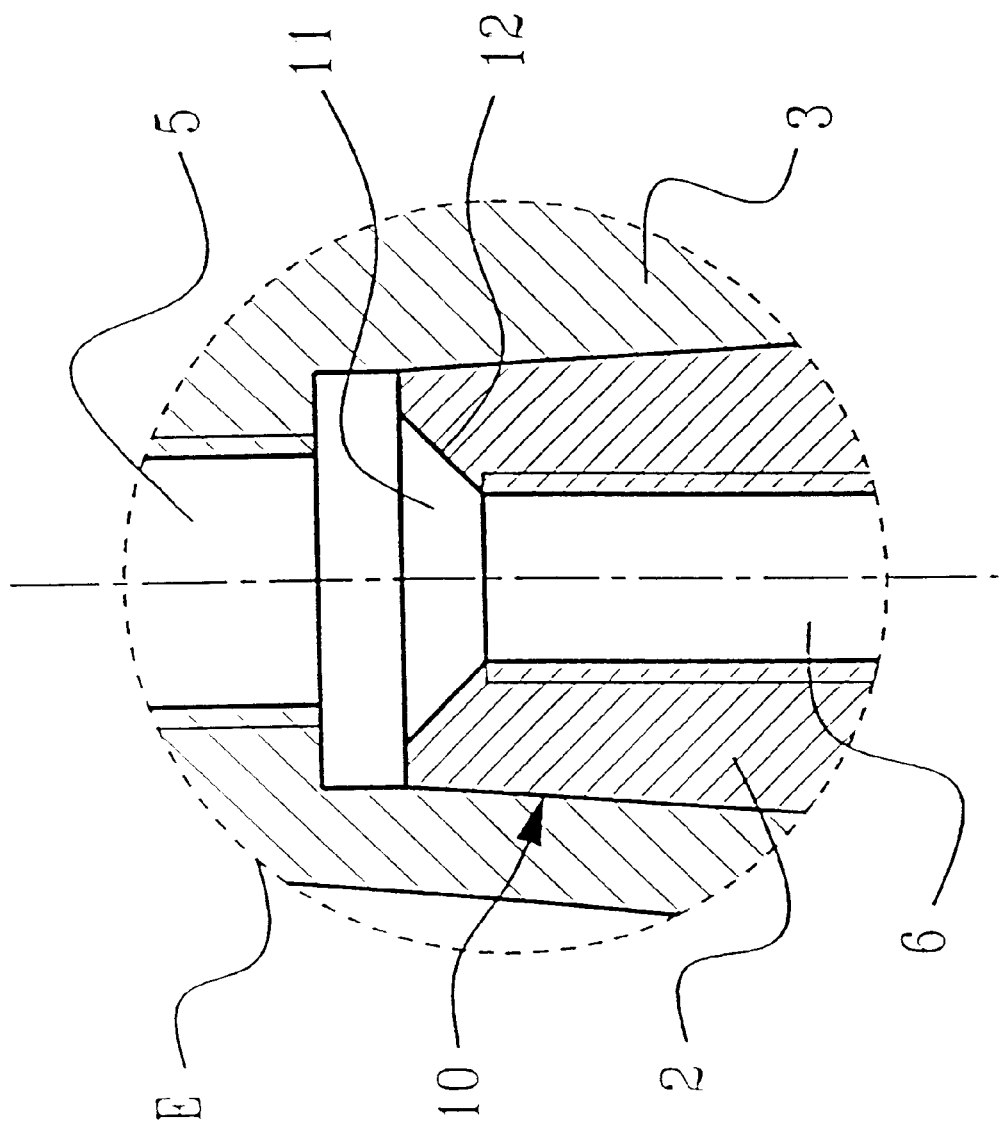
FIG. 3 is an enlarged view of the detail E in FIG. 1.

The detail E of FIG. 1, shown on a larger scale in FIG. 3, illustrates an advantageous further feature of the invention shown in FIGS. 1, 1$a$ and 2. To prevent an effective intervention of the screw bolt (not shown) on the top side of the proximal end of the succeeding shaft part 2 from damaging the threaded portion 6 provided there, a recess 11 embodied as a chamfer is provided on the proximal end of the threaded bore. The inclination of the flanks 12 amounts to 45° and corresponds to the inclination of the flanks of the chamfer on the threaded end of the screw bolt (not shown). As a result, an optimal introduction of force into the succeeding shaft part 2 can be accomplished, in order to enable loosening the conical insert connection 10 between the succeeding shaft part 3 and head part 2 with a relatively slight exertion of force. In this way, the head part can be removed from an implanted shaft, if a later operation should become necessary, without a substantial exertion of force and with only slight reaction forces. This makes it quite certain that the shaft part that remains in the bone will not loosen or come out of the bone.

It will be appreciated that—in further embodiments not shown in the drawing—by means of the attained modularity in a system of shaft prostheses for attaining different individually dimensioned prosthesis forms, various sizes of elements can be combined with one another. The graduation in thread diameters provided according to the invention can likewise be provided between different successive elements. Thus it is possible to achieve a division—if desired—not only between the head part and the distally succeeding shaft part but also between different shaft parts, for instance. For purposefully "dialing up" a connection that is to be released, with thread diameters that increase in stages toward the head end, one would then have to look for a bolt whose male thread comes into engagement with the female thread, which comes into engagement with the shaft element located on the proximal side of the intended dividing point. It is then braced by the edge of its end on the edge of the bore of the distally adjacent element and separates the selected connection.

In a modular system with differently curved shaft elements, individually shaped shafts can be created by means of different relative angle positioning, without in any way limiting the releasability of the connection as described above.

The invention is not limited in its realization to the preferred exemplary embodiment described above. On the contrary, a number of variants are conceivable, which make use of the provisions described, even in fundamentally different types of embodiments.

What is claimed is:

1. A modular joint prosthesis having a head part and at least one shaft part which can be connected by means of an insertable cone connection, wherein a bore is provided that extends essentially coaxial to a longitudinal axis of the shaft part and extends through the head part and at least one section of the shaft part, said bore having a first segment with a first diameter and a first inside thread in the head part, and a second segment with a second inside thread in the shaft part and a second diameter which is 1.5 to 2.5 times smaller than the first diameter, so as to define circular ring on the shaft part between the first and second segments, whereby a screw means, screwed into the first inside threads, can generate an axially oriented pressure force on the circular ring to sever the insertable cone connection; and a tie rod having a proximal end, said tie rod being inserted into the bore and screwed into the second inside thread in order to set and secure the insertable cone connection, until the proximal end of the tie rod is supported on the head part.

2. The joint prosthesis of claim 1, wherein the first inside thread and the second inside thread extend over the entire length of their respective segments of the bore.

3. The joint prosthesis of claim 1, wherein the shaft part has a proximal end adjacent a region where the shaft part connects to the head part and the second inside thread is provided only in the region of the proximal end.

4. The joint prosthesis of claim 1, wherein the bore of the second segment has a chamfer which is adjacent the first segment of the bore.

5. The joint prosthesis of claim 4, wherein the chamfer has an angle of inclination of approximately 45°, with regard to a center axis of the second segment.

6. The joint prosthesis of claim 1, wherein the head part further includes a joint connection cone on a medial side of the head part; and a channel recess below the joint connection cone, said channel recess having an arc-shaped boundary.

7. A kit for making a modular joint prosthesis, comprising:

a selection of head parts having at least one of a different length and a different diameter; and a selection of shaft parts having at least one of a different length, a different diameter and a different curvature where the head parts and the shaft parts are connected by means of an insertable cone connection, and a bore is provided that extends essentially coaxial to a longitudinal axis of a shaft part and extends through a head part and at least one section of the shaft part, said bore having a first segment with a first diameter and a first inside thread in the head part, and a second segment with a second inside thread in the shaft part and a second diameter which is 1.5 to 2.5 times smaller than the first diameter so as to define a circular ring on the shaft part between the first and second segments; and a tie rod that can be inserted into the bore and screwed into the second inside thread in order to set and secure the insertable cone connection, until the proximal end of the tie rod is supported on the head part.

8. A kit of claim 7 wherein a diameter in the range from 12 to 17 mm is contemplated for the head parts, and a length range from 200 to 320 mm and a diameter range from 10 to 14 mm are provided for the shaft parts.

* * * * *